(12) United States Patent
Sharpless et al.

(10) Patent No.: US 6,271,400 B2
(45) Date of Patent: *Aug. 7, 2001

(54) EPOXIDATION OF OLEFINS

(75) Inventors: K. Barry Sharpless, La Jolla, CA (US); Andrei K. Yudin, Toronto (CA)

(73) Assignee: The Scripps Research Institute, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,393

(22) Filed: Oct. 23, 1998

Related U.S. Application Data

(60) Provisional application No. 60/062,760, filed on Oct. 23, 1997.

(51) Int. Cl.$^7$ .......................... C07D 301/03; B01J 31/22

(52) U.S. Cl. .......................... 549/525; 502/152; 502/150

(58) Field of Search ............................ 549/525; 502/152, 502/150

(56) References Cited

FOREIGN PATENT DOCUMENTS

97/32867 * 9/1997 (WO) .................................. 549/525

OTHER PUBLICATIONS

Dannley, et al., "the Synthesis of Silyl Hydroperoxides and Bissilyl Peroxides", *J. Org. Chem. 30*: 2417–2419 (1965).
Rebek, et al., "New Epoxidation Reagents Derived form Alumina and Silicon", *Tetrahedron Lett*: 4337–4338 (1979).
Warwel, et al., "Formation of Vicinal Diols by $Re_2O_2$–Catalyzed Hydroxylation of Alkenes with Hydrogen Peroxide", *Chem. Commun.*: 1578–1579 (1991).
Hermann, et al., "Alkyl–and Arylrhenium Trioxides", *Angew. Chem. Int. Ed. Engl. 30*: 185–187 (1991).
Hermann, et al., "Methyltrioxorhenium as Catalyst for Olefin Oxidation", *angew. Chem. Int. Ed. Engl. 30*: 1638–1641 (1991).
Hermann, et al., "Methyltrioxorhenium(VII) as Catalyst for Epoxidations: Structure of the Active Species and Mechanism fo Catalysis", *Angew. Chem. Int. Ed. Engl. 32*: 1157–1160 (1993).
Hermann, et al., "Alkrylrhenium Oxides as Homogenous Epoxidation Catalysts: Activity, Selectivity, Stability, Deactivation", *J. Mol. Catal. 86*: 243–266 (1994).
Hermann, et al., "Essays on Organometallic Chemistry, VII, Laboratory Curiosities of Yesterday, Catalysis of Tomorrow: Organometallic Oxides", *J. Organomet. Chem. 500*: 149–174 (1995).

(List continued on next page.)

*Primary Examiner*—C. S. Aulakh
(74) *Attorney, Agent, or Firm*—Donald G. Lewis

(57) ABSTRACT

An process for epoxidizing diversely functionalized olefins by oxorhenium catalysis employs conditions which control water concentration. By controlling water concentration, one can maximize monoperoxo complex formation and increase turnover which subsequently reduces diol side products obtained from epoxide ring opening and increases the yield of the desired epoxide product. The optimal range of water concentrations is 0.50–80.0 mol %. Using less than 0.5 mol % water does not result in practical turnovers and 1.0 equivalent of water (or more) is detrimental to the lifetime of the active catalytic species formed. More particularly, there are four aspects to controlling water concentration: 1) anhydrous oxidants using trialkylsilyl peroxides and an in situ source of BTSP eliminating the need for its isolation; 2) water removal agents including molecular sieves (Aldrich, 3 Å, 4 Å) and common inorganic dehydrating agents; 3) rhenium catalysts; and 4) a boiling reactor process in the context of oxorhenium catalyzed epoxidation.

16 Claims, 6 Drawing Sheets

OTHER PUBLICATIONS

Al–Ajlouni, et al., "Epoxidation of Styrenes by Hydrogen Peroxide as Catalyzed by methylrhenium Trioxide", *J. Am. Chem. Soc. 117*: 9243–9250 (1995).

Hermann, et al., "The Peroxo Perrhenic Acid $H_4Re_2O_{13}$: An Oxygen–Rich Metal Peroxide and Oxidation Catalyst", *Chem. Eur. J. 2*: 168–173 (1996).

Adam, et al., "Methyltrioxorhenium(VII)–Catalyzed Epoxidation of Alkenes with the Urea/Hydrogen Peroxide Adduct", *Angew. Chem. Int. Ed. Engl. 35*: 533–535 (1996).

Al–Ajlouni, et al., "Kinetics and Mechanism of the Epoxidation of Alkyl–Substituted Alkenes by Hydrogen Peroxide, Catalyzed by Methylthenium Trioxide", *J. Org. Chem. 61*: 3969–3976 (1996).

Hermann, et al., "Multiple Bonds Between Transition Metals and Main–Group Elements: Part 161 Oxygen–Donor Adducts of Organorhenium(VII) Oxides: Syntheses, Structures, and Catalytic Properties", *J. Mol. Catal. 118*: 33–45 (1997).

Barron, et al., "the Selective Functionalization of Saturated Hydorcarbons. Part 37. Utilization of a New Oxidant: Bis(t-rimethylsilyl) Peroxide", *Tetrahedron 53*: 487–510 (1997).

Barton, et al., "The Selective Functionalization of Saturated Hydrocarbons. Part 38. Bis(trimethylsilyl) Peroxide: an Efficient Oxidant for the Functionalization of Hydrocarbons Involving the $Fe^{IISM}Fe^{IV}$ Manifold", *Tetrahedron 53*: 511–520 (1997). Hermann, et al., "Multiple Bonds Between Transition Metals and Main–Group Elements Part 168. methyltrioxorhenium/Lewis base Catalysts in Olefin Epoxidation", *J. Organomet. Chem. 549*: 319–322 (1997).

Rudolph, et al., "Highly Efficient Epoxidation of Olefins Using Aqueous $H_2O_2$ and Catalytic Methyltrioxorhenium/Pyridine: Pyridine–Mediated Ligand Acceleration", *J. Am. Chem. Soc. 119*: 6189–6190 (1997).

Copcret. et al., "A Simple and Efficient Method for Epoxidation of Terminal Alkenes", *Chem. Commun.*: 1565–1566 (1997).

* cited by examiner

A)
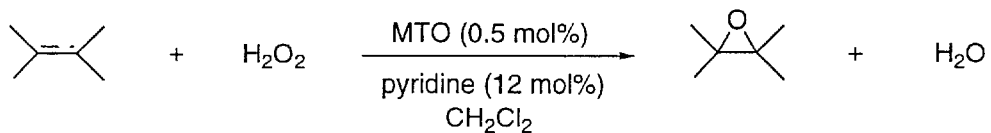
B)
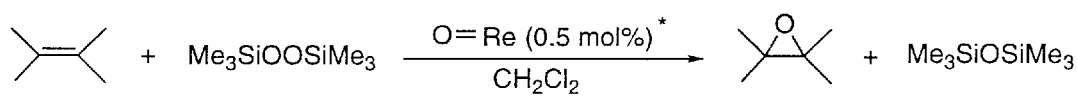
*effective catalysts include MTO, $Re_2O_7$, $ReO_3(OH)$, and $ReO_3$
C)
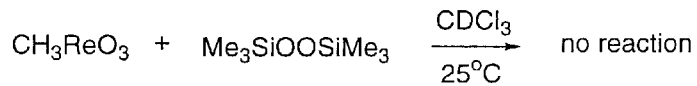
FIGURE 1

| Entry[a,b] | Olefin | Catalyst Precursor[c]/ Solvent | Time (h) | Isolated Yield (%) |
|---|---|---|---|---|
| 1 | (4-octene) | A / $CH_2Cl_2$<br>B / $CH_2Cl_2$<br>C / $CH_2Cl_2$ | 15<br>20<br>12 | 92<br>90<br>88 |
| 2 | (2-decene) | A / $CH_2Cl_2$<br>D / $CH_2Cl_2$<br>F / $CH_2Cl_2$ | 9<br>16<br>11 | 90<br>85<br>79 |
| 3 | (1-decene) | D / $CH_2Cl_2$<br>D / neat | 14<br>8 | 94<br>83 |
| 4 | (hexenenitrile) | D / $CH_2Cl_2$ | 18 | 92 |
| 5 | (vinylcyclohexane) | D / $CH_2Cl_2$ | 7 | 95 |
| 6 | (stilbene) | D / THF | 10 | 96 |
| 7 | | E / THF<br>G / THF | 12<br>10 | 68<br>82 |
| 8[d] | (1,5-cyclooctadiene) | G / THF | 13 | 78 |
| [e] | (1,3-cyclooctadiene) | | | |

FIGURE 2

A)
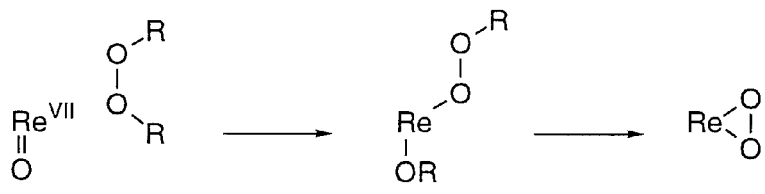
R = H or SiMe$_3$
B)
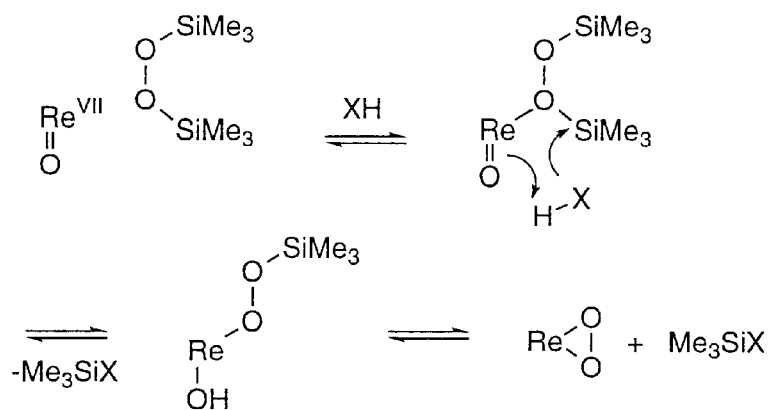
X = OH, OSiMe$_3$
FIGURE 4

| Entry | Alkene | Catalyst Precursor/c Solvent | Yield, % | Time, h |
|---|---|---|---|---|
| 1 | CH₂=CH-(CH₂)₅-CH₃ | A / CH₂Cl₂ | 94 | 14 |
| 2 | CH₂=CH-(CH₂)₃-CN | A / CH₂Cl₂ | 92 | 18 |
| 3 | CH₂=CH-CH₂-CH₂-Br | B / CH₂Cl₂ | 82 | 9 |
| 4 | CH₂=CH-C(CH₃)₂-CO₂Me | B / CH₂Cl₂ | 77 | 15 |
| 5 | CH₂=CH-CH₂-CH₂-OAc | B / CH₂Cl₂ | 82 | 3 |
| 6 | CH₂=CH-CH₂-Ph | B / CH₂Cl₂ | 88 | 9 |
| 7 | allyl-C₆F₅ | C / CH₂Cl₂ | 90 | 15 |
| 8 | vinylcyclohexane | A / CH₂Cl₂ | 95 | 7 |
| 9 | BnO-CH₂-CH=CH₂ | B / CH₂Cl₂ | 95 | 8 |
| 10 | cis-3-hexene | D / CH₂Cl₂<br>E / CH₂Cl₂ | 88<br>80 | 12<br>18 |
| 11 | trans-2-nonene | B / CH₂Cl₂<br>F / CH₂Cl₂ | 90<br>85 | 9<br>9 |

FIGURE 5

| Entry | Alkene | Catalyst Precursor/c Solvent | Yield, % | Time, h |
|-------|--------|------------------------------|----------|---------|
| 12 | Ph-CH=CH-Ph (trans-stilbene) | A / THF | 96 | 10 |
| 13 | CH₃CH₂CH=CHCH₂CO₂Me | B / CH₂Cl₂ | 90 | 3 |
| 14 | (CH₃)₃C-CH=CH-CH₂CH₂CH₃ | B / CH₂Cl₂ | 70 | 4 |
| 15 | (Et)(nPr)C=CH-CH₂CH₂CH₃ | B / CH₂Cl₂ | 96 | 4 |
| 16 | (CH₃)₂C=CH-(CH₂)₉CH₃ | B / CH₂Cl₂ | 81 | 14 |
| 17 | (CH₃)₂C=C(CH₃)-CH₂CH₂CH₃ | B / CH₂Cl₂ | 82 | 14 |
| 18 | 1,5-cyclooctadiene | A / CH₂Cl₂ | 82 | 10 |
| 19 | cyclooctene | A / CH₂Cl₂ | 78 | 13 |

FIGURE 6

EPOXIDATION OF OLEFINS

RELATED APPLICATIONS

The present application claims priority from Provisional Application Ser. No. 60/062,760, filed Oct. 23, 1997. +gi

GOVERNMENT RIGHTS

This invention was made with government support under Grant No. GM 28384 awarded by the National Institutes of Health and Grant No. CHE 9531152 awarded by the National Science Foundation. The U.S. government has certain rights in the invention.

TECHNICAL FIELD

The invention is directed to an improved method for the oxorhenium catalyzed epoxidization of diversely functionalized olefins wherein the improvement comprises conditions which control water concentration.

BACKGROUND

In recent years, the chemistry pertaining to the selective oxidation of olefins was dominated by $OsO_4$ and $O_3Os=N—X$ species, the essential reactants in the catalytic asymmetric dihydroxylation (AD) and aminohydroxylation (AA) processes, respectively (Kolb et al. Chem. Rev. 1994, 94, 2483; Schlingloff et al. in Asymmetric Oxidation Reactions: A Practical Approach, Katsuki, T., Ed.: Oxford University Press, in press). Our continuing search for new transition metal-catalyzed heteroatom transfer reactions has centered around osmium's neighbors in the Periodic Table. Among the corresponding high valent oxo derivatives, methylrhenium trioxide ($CH_3ReO_3$ or MTO) has been known for a long time (Beattie et al. Inorg. Chem. 1979, 18, 2318). It was only recently, however, that Herrmann and others developed MTO into a well defined catalyst for a variety of processes including olefin epoxidation with aqueous hydrogen peroxide ($H_2O_2$). For applications of MTO in organic synthesis, see: Hoechst AG (Herrmann et al. ) DE 3.902.357 (1989); Herrmann et al. Angew. Chem., Int. Ed. Engl. 1991, 30, 1638; Herrmann et al. J. Mol. Catal. 1994, 86, 243; Herrmann et al. Organomet. Chem. 1995, 500, 149; Al-Ajlouni et al. Am. Chem. Soc. 1995, 117, 9243; Pestovsky et al. J. Chem. Soc., Dalton Trans. 2 1995, 133; Adam et al. Angew. Chem. Int. Ed. 1996, 35, 533; Boelow et al. Tetrahedron Lett. 1996, 37, 2717; Al-Ajlouni et al. J. Org. Chem. 1996, 61, 3969; Herrmann et al. J. Mol. Cat. 1997, 118, 33; Herrmann et al. Acc. Chem. Res. 1997, 30, 169; Espenson et al. Adv. Chem. Ser. 1997, 253, 99; ARCO Chemical Technology (Crocco et al., H. S.) U.S. Pat. No. 5,166,372 (1992).

Regarding olefin oxidation, there is a fundamental. difference between OsO4 and $CH_3ReO_3$, for in contrast to $OsO_4$, MTO does not react directly with olefins (This is true regarding olefin epoxidation. However, MTO is known to exhibit metathesis activity (Herrmann et al. Acc. Chem. Res. 1997, 30, 169). Rather, the MTO-catalyzed epoxidation is believed to proceed through the initial activation of $H_2O_2$ by the electrophilic Re(VII) center resulting in the formation of equilibrating mixture of mono- and bisperoxorhenium complexes that transfer oxygen atoms to the corresponding olefins. Notably, the $OsO_4/H_2O_2$ system has little synthetic value for olefin epoxidation. Even though epoxides are the primary products in this system, significant amounts of diols and overoxidation products are formed (Milas et al. J. Am. Chem. Soc. 1936, 58, 1302).

The major limitation of Herrmann's original $MTO/H_2O_2$ epoxidation system is the acidity of the reaction medium. The water molecule coordinated to the Re(VII) center of the bisperoxo complex is highly acidic and sensitive epoxides do not survive (The water molecule coordinated to the rhenium center of the bisperoxo complex of MTO is highly acidic: Herrmann et al. Angew. Chem. Int. Ed. Eng. 1993, 103, 1991). Recent efforts in our laboratory led to a highly efficient olefin epoxidation with 30% aqueous $H_2O_2$ where the catalytic activity of MTO was uncoupled from acidity for the first time (Rudolph et al. J. Am. Chem. Soc. 1997, 119, 6189; Coperet et al. Chem. Commun. 1997, 16, 1565). The crucial features of this new process are the requirement for a pyridine ligand and the solvent switch from tert-butyl alcohol to methylene chloride which additionally enhances the effectiveness of the pyridine-modified rhenium catalyst (FIG. 1A).

We have previously disclosed on further improvements in this epoxidation catalysis, specifically on the use of 3-cyanopyridine as a ligand of choice for the epoxidation of terminal and trans-disubstituted olefins (Coperet et al. Chem. Commun. 1997, 16, 1565).

What is needed is an efficient and improved method for oxorhenium epoxidization of diversely functionalized olefins wherein the improvement increases turnover and which subsequently reduces diol side products obtained from epoxide ring opening and increases the yield of the desired epoxide product.

SUMMARY one aspect of the invention is directed to an improved process for epoxidizing olefins by rhenium-catalysis. More particularly, the rhenium-catalyzed epoxidation is of a type wherein a reaction mixture is formed by combining the olefin with a ligand, a solution of oxidant, an organic solvent, a protic solvent and a catalytic organo rhenium oxide under conditions suitable for epoxide formation to occur. The improvement is directed to the use of a a silicon based anhydrous oxidant and to its controlled slow addition to the reaction mixture. In a preferred embodiment, the silicon based anhydrous oxidant is a trialkylsilyl peroxide represented by the formulas $(R)_3SiOOSi(R)_3$, and $(—(R)_2SiOO—)_n$. In the above formulas, R is selected from the group consisting of $C_1–C_6$ alkyl and tert-$C_1–C_6$ alkyl. A preferred silicon based anhydrous oxidant is bis (trimethylsilyl) peroxide. During the slow addition of the silicon based anhydrous; oxidant, a peroxo group is transferred from the oxidant to the rhenium oxide with the assistance of the protic solvent, thereby controlling excess water concentration and maximizing monoperoxocomplex formation.

A further aspect of the invention is directed to the addition of a water removal agent to the reaction mixture. Preferred water removal agents include a group consisting of Molecular sieves (Aldrich, 3 Å, 4 Å), $MgSO_4$, $Na_2SO_4$, $NaSO_4$, $CaCl_2$, $K_2CO_3CaO$, $P_2O_5$. Preferred rhenium catalysts include $(R)ReO_3$, $Re_2O_7$, $ReO_3$, $ReO_3$ (OH), $HReO_4$, $NH_4ReO_4$, Re (metal), $ReO_2$, and $Me_3SiOReO_3$. In the above formulas, R may be selected from the group consisting of $C_1–C_6$ alkyl and tert-$C_1–C_6$ alkyl.

A further aspect of the invention is directed to the removal of product water formed during the reaction process. Product water is removed from the reaction mixture by use of a boiling reactor process for maintaining an aqueous concentration in the reaction mixture low enough for retaining activity of the oxorhenium catalyst.

In a preferred mode, the olefin is a mono-substituted olefin, a di-substituted olefin, a tri-substituted olefin, or a tetra-substituted olefin. Preferred ligands include the following: pyridine, pyridine derivatives containing electron withdrawing or electron donating groups (nitro, esters, ketones, halogens, nitriles, sulphonic acid esters), chiral pyridines (like cotinine), imines, oxazolines, 2-methylpyridine (2-picoline), 2-ethylpyridine, 2-propylpyridine, 2-phenylpyridine, 2-benzylpyridine, 2-fluoropyridine, 2-chloropyridine, 2-bromopyridine, 2-cyanopyridine, 2-hydroxypyridine, 2-pyridylcarbinol, 2-pyridineethanol, 2-pyridinepropanol, pyridine-2-carboxylic acid (picolinic acid) and corresponding esters, 3-methylpyridine (3-picoline), 3-ethylpyridine, 3-butylpyridine, 3-phenylpyridine, 3-benzylpyridine, 3-fluoropyridine, 3-chloropyridine, 3-bromopyridine, 3-cyanopyridine, 3-pyridylcarbinol, 3-hydroxypyridine, 3-pyridinepropanol, pyridine-3-carboxylic acid (nicotinic acid) and corresponding esters, 4-methylpyridine (4-picoline), 4-fluoropyridine, 4-chloropyridine, 4-bromopyridine, 4-cyanopyridine, 4-ethylpyridine, 4-isopropylpyridine, 4-t-butylpyridine, 4-(1-butylpentyl)pyridine, 4-phenylpyridine, 4-benzylpyridine, 4-(4-chlorobenzyl)pyridine, 4-hydroxypyridine, 4-methoxypyridine, 4-nitropyridine, pyridine-4-carboxylic acid and corresponding esters, 2,3-dimethylpyridine (2,3-lutidine), 2,4-dimethylpyridine (2,4-lutidine), 2,5-dimethylpyridine (2,5-lutidine), 2,6-dimethylpyridine (2,6-lutidine), 3,4-dimethylpyridine (3,4-lutidine), 3,5-dimethylpyridine (3,5-lutidine), 2,6-difluoropyridine, pentafluoropyridine, pentachloropyridine, 2,6-dichloropyridine, 3,5-dichloropyridine, 2,3,5-trichloropyridine, 3,4-dicyanopyridine, 5-chloro-3-pyridinol, 2,3-pyridinecarboxylic acid and corresponding esters, 2,4-pyridinecarboxylic acid and corresponding esters, 2,5-pyridinecarboxylic acid and corresponding esters, 2,6-pyridinecarboxylic acid and corresponding esters, 2,6-diphenylpyridine, 2,6-di-p-tolylpyridine, 3,4-pyridinecarboxylic acid and corresponding esters, 2-pyridineethansulfonic acid, 4-pyridineethanesulfonic acid, 2,3-cyclopentenopyridine, 2,3-cyclohexenopyridine, 2,3-cycloheptenopyridine, 2,4,6-collidine, pyrazine, 2,3-pyrazinedicarbonitrile, pyrazinecarbonitrile, 2,6-dichloropyrazine, pyrazinecarboxylic acid and corresponding esters, 2,3-dimethylpyrazine, 2,5-dimethylpyrazine, 2,6-dimethylpyrazine, 2,3-di-2-pyridylpyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 1,3,5-triazine, (−)-cotinine (1-methyl-5-(3-pyridyl)-2-pyrrolidinone)pyridine-2,6-dicarboxylic acid and corresponding esters, quinoline, isoquinoline, 2,2'-pyridyl, 2,2'-dipyridyl, 6-chloro-2,2'-bipyridine, 2,4'-dipyridyl, 4,4'-dipyridyl, 2,2':6',2''-terpyridine, 1,7-phenanthroline, 1,10-phenanthroline, 4,7-phenanthroline, phenazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-nitropyrazole, 2,5-diphenyloxazole, 2,4,5-trinethyloxazole, 2,4,4-trimethyl-2-oxazoline, 3,5-dimethylisoxazole, 2,6-bis[(4S)-isopropyl-2-oxazolin-2-yl]pyridine, 1,2-dimethylimidazole, 1-butylimidazole, 2,3,3-trimethylindolenine, and caffeine. Preferred solvents include nitromethane ($CH_3NO_2$), nitroethane ($EtNO_2$), methylene chloride ($CH_2Cl_2$), chloroform ($CHCl_3$), carbon tetrachloride ($CCl_4$), 1,2-dichloroethane ($CH_2ClCH_2Cl$), pentachloroethane ($CCl_3CHCl_2$), chlorinated aromatic compounds: chlorobenzene, dichlorobenzene and other chlorinated solvents, fluorinated solvents and chlorofluoro hydrocarbons, acetonitrile ($CH_3CN$), acetone, benzene, toluene, xylenes, methanol, ethanol, propanol, isopropanol, butanol, t-butanol, ethyleneglycol, diethylether, THF (tetrahydrofuran) and supercritical $CO_2$. In a preferred mode, the ligand is present in 0.25 to 1.0 mol % overall concentration; alternatively, the ligand may be present in 0.25 to 12.0 mol % overall concentration. A preferred overall water concentration is within the range of 0.5–80.0 mol %.

DESCRIPTION OF FIGURES

FIG. 1 illustrates (a) shows the preferred mode of the MTO epoxidation employing a pyridine ligand and methylene chloride as the solvent; (b) shows the improvement viz.: replacement of aqueous H2O2 with bis(trimethylsilyl) peroxide (BTSP) as an oxygen atom source; (c) shows that MTO shows little to no reactivity toward BTSP in $CDCl_3$.

FIG. 2 shows a table of olefins (indicated entries) wherein epoxidation of olefins with bis(trimethylsilyl)peroxide(btsp) was catalyzed by high valent oxorhenium derivatives with the following conditions: (a) 10 mmol scale; (b) 1.5 eq BTSP per double bond was used; (c) A: $CH_3ReO_3$ (0.5 mol %), pyridine (1 mol %); B: $CH_3ReO_3$ (0.25 mol %), pyridine (0.5 mol %); C: $Re_2O_7$ (0.5 mol %), pyridine (1 mol %); D: $Re_2O_7$ (0.5 mol %); E: $HReO_4$ (0.5 mol %); F: $ReO_3$ (0.5 mol %); G: $Re_2O_7$ (1 mol %); (d) syn-diepoxide was obtained (>99:1); (e) anti-diepoxide was obtained (>99:1).

FIG. 4 illustrates A) (in the case of BTSP) formation of peroxo complexes which must be accompanied by the silylation of the rhenium-bound oxo ligand wherein this process is apparently much slower than its protic counterpart; B) the need for a proton source is accommodated where a regenerable XH species helps in ferrying the peroxo group from silicon to rhenium.

FIG. 5 defines the scope of the oxorhenium process with representative substrates including fairly unreactive olefins and/or progenitors of sensitive epoxides with the following conditions a) 10 mmol scale; (b) 1.5 eq BTSP per double bond was used; (c) A: $Re_2O_7$ (0.5 mol %), $H_2O$ (5 mol %); B: $ReO_3$ (0.5 mol %), $H_2O$ (5 mol %); C: $ReO_3$ (0.5 mol %), $H_2O$ (1 mol %); D: $Re_2O_7$ (0.5 mol %), pyridine (1 mol %), $H_2O$ (5 mol %); E: $2py/HReO_4$ (0.5 mol %), $H_2O$ (5 mol %); F: MTO (0.5 mol %), $H_2O$ (5 mol %).

FIG. 6 defines the scope of the oxorhenium process with representative substrates including fairly unreactive olefins and/or progenitors of sensitive epoxides with conditions as described in FIG. 5.

DETAILED DESCRIPTION OF THE INVENTION

Figure 3:
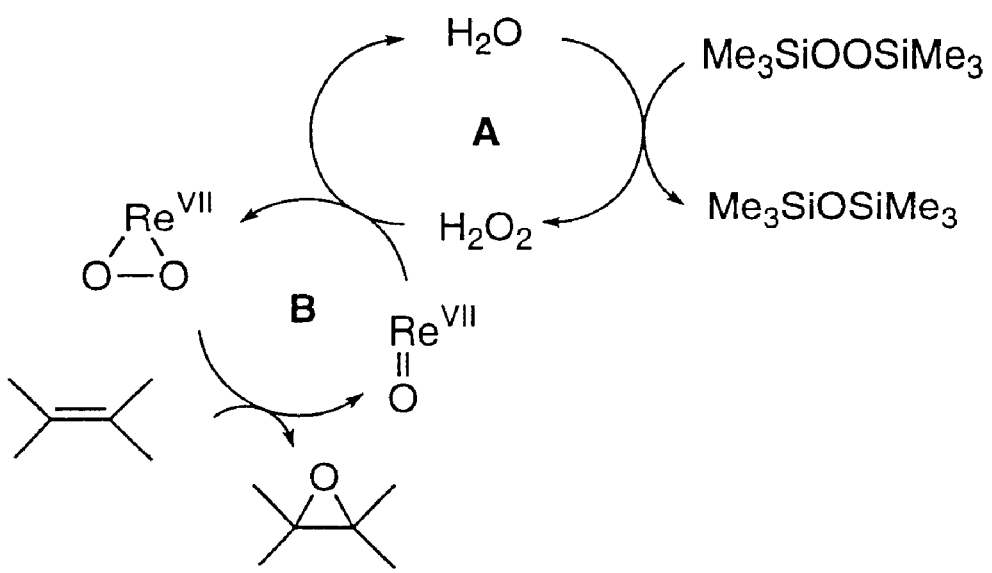
FIG. 3 shows basis for the observations that a trace of water in the reaction mixture hydrolyzes BTSP to hydrogen peroxide which subsequently adds to the rhenium center producing the peroxo complex while releasing a water molecule which closes the oxidant regeneration loop.

The invention is directed to an improved method for oxorhenium catalyzed epoxidization of diversely functionalized olefins wherein the improvement comprises conditions which control water concentration. By controlling water concentration, one can maximize monoperoxo complex formation and increase turnover which subsequently reduces diol side products obtained from epoxide ring opening and increases the yield of the desired epoxide product. The optimal range of water concentrations is 0.50–80.0 mol %. Using less than 0.5 mol % water does not result in practical turnovers and 1.0 equivalent of water (or more) is detrimental to the lifetime of the active catalytic species formed. More particularly, there are four aspects to controlling water concentration:

1. Anhydrous Oxidants

Trialkylsilyl peroxides $R_3SiOOSiR_3$; note that drying agents or continuous water removal technologies are employed for BTSP ($R_3SiOOSiR_3$) epoxidation); related trialkylsilyl hydroperoxides $R_3SiOOH$ (see attached material for the preparation) and polymeric derivatives $(-R_2SiOO-)_n$ (R=organic functionality, see attached material for the preparation);

bis(tert-butyl)peroxide (Aldrich) and benzoyl peroxide (Aldrich) in combination with hexamethyldisilazane (Aldrich) (in situ source of BTSP eliminating the need for its isolation), tert-butyl hydroperoxide (Aldrich);

2. Water Removal Agents

Molecular sieves (Aldrich, 3 Å, 4 Å);

common inorganic dehydrating agents including $MgSO_4$, $Na_2SO_4$, $CaSO_4$, $CaCl_2$, $K_2CO_3$, $CaO$, $P_2O_5$. (all Aldrich).

3. Rhenium Catalysts $RReO_3$ (for example, $CH_3ReO_3$), $Re_2O_7$, $ReO_3$, $HReO_4$, $NH_4ReO_4$, Re (metal), $ReO_2$ (All Aldrich), $Me_3SiOReO_3$ (Strem)

4. Boiling Reactor Process.

The boiling reactor process, in the context of oxorhenium catalyzed epoxidation, comprises a method which continuously removes water in the vapor stream by using appropriate solvent, temperature, and pressure conditions, keeping the concentration of the liquid phase low enough to maintain the activity of the oxorhenium catalyst.

EXAMPLE 1

Bis(trimethylsilyl) Peroxide Extends the Range of Oxorhenium Catalysts for Olefin Epoxidation We disclose hereiin further improvements in the epoxidation catalysis, the most significant being replacement of the organometallic rhenium species (e.g. MTO) by cheaper and more stable inorganic rhenium oxides (e.g. $Re_2O_7$, $ReO_3$(OH) and $ReO_3$).

Among the known organometallic oxorhenium (VII) species (R—$ReO_3$) capable of catalyzing olefin epoxidation, MTO appears to be the most stable toward oxidative and/or hydrolytic removal of the alkyl group (vide infra; For a comprehensive study on the base-induced decomposition of MTO, see: Abu-Omar et al. J. Am. Chem. Soc. 1996, 118, 4966. In the presence of pyridine and $H_2O_2$, MTO is slowly oxidized, producing pyridinium perrhenate and $CH_3OH$: Yudin, A. K.; Sharpless, K. B. unpublished results).

Hence, catalyst modification by variation of the R-substituent on the rhenium center was not rewarding despite extensive efforts in the Herrmann laboratory. In addition, R—$ReO_3$ compounds, including MTO, are quite expensive (For applications of MTO in organic synthesis, see: (a) Hoechst AG (Herrmann, W. A.; Marz, D. W.; Kuchler, J. G.; Weichselbaumer, G.; Fischer, R. W.) DE 3.902.357 (1989); (b) Herrmann et al. Angew. Chem., Int. Ed. Eng. 1991, 30, 1638. (c) Herrmann et al. J. Mol. Catal. 1994, 86, 243; (d) Herrmann et al. J. Organomet. Chem. 1995, 500, 149; (e) Al-Ajlouni et al. J. Am. Chem. Soc. 1995, 117, 9243; (f) Pestovsky et al. J. Chem. Soc., Dalton Trans. 2 1995, 133; (g) Adam et al. Angew. Chem. Int. Ed. 1996, 35, 533; (h) Boelow et al. Tetrahedron Lett. 1996, 37, 2717; (i) Al-Ajlouni et al. J. Org. Chem. 1996, 61, 3969; (j) Herrmann et al. J. Mol. Cat. 1997, 118, 33; (k) Espenson et al. Adv. Chem. Ser. 1997, 253, 99; (l) ARCO Chemical Technology (Crocco, G. L.; Shum, W. P.; Zajacek, J. G.; Kesling Jr., H. S.) U.S. Pat. No. 5,166,372 (1992). Herrmann et al. Acc. Chem. Res. 1997, 30, 169. The most practical preparation of MTO to date involves the reaction of tetramethyltin, $Re_2O_7$, and hexafluoroglutaric anhydride in acetonitrile: Herrmann et al. Inorg. Chem. 1992, 31, 4431.

These factors provided the incentive to seek water-free epoxidation conditions which would hopefully extend the lifetime of the MTO catalyst. This goal and much more was accomplished by simply replacing aqueous $H_2O_2$ with bis (trimethylsilyl)peroxide (BTSP) as an oxygen atom source (FIG. 1B) ((a) Cookson et al. J. Organomet. Chem. 1975, 99, C31; (b) Taddei, M.; Ricci, A. Synthesis 1986, 633; (c) for a convenient, large-scale preparation of BTSP from bis (trimethylsilyl)urea and urea/$H_2O_2$ complex in dichloromethane, see: Jackson, W. P. Synlett 1990, 536. The product obtained according to this method is virtually free of hexamethyldisiloxane, a common by-product in cognate BTSP preparations (see Supporting Material for details of a one mole preparation); (d) Babin et al. Synth. Commun. 1992, 22, 2849.

Thermal stabilities of silylated organic peroxides have been studied: Vesnovskii, B. P.; Thomadze, A. V.; Suchevskaya, N. P.; Aleksandrov, Yu. A. Zh. Prikl. Khim. 1982, 55, 1005. We would like to stress, however, that despite its great thermal stability, BTSP is subject to facile hydrolysis in the presence of water and acids which could result in formation of hazardous 100% $H_2O_2$. However, pure BTSP has an active oxygen content of only 9% (cf. tert-butyl hydroperoxide—17.8%; di-tert-butyl peroxide—10.9%; hydrogen peroxide—47%). For applications of BTSP in organic synthesis, see: (a) Brandes, D.; Blaschette, A. J. Organomet. Chem. 1973, 49, C6; (b) Brandes, D.; Blaschette, A. ibid. 1974, 73, 217; (c) Tamao, K.; Kumada, M.; Takahashi, T. ibid. 1975, 94, 367; (d) Salomon, M. F.; Salomon, R. G. J. Am. Chem. Soc. 1979, 101, 4290; (e) Adam, W.; Rodriguez, A. J. Org. Chem. 1979, 44, 4969; (f) Suzuki, M.; Takada, H.; Noyori, R. ibid. 1982, 47, 902; (g) Weber, W. P. "Silicon Reagents in Organic Synthesis," Springer-Verlag: New York, 1983; (h) Kanemoto, S.; Oshima, K.; Matsubara, S.; Takai, K.; Nozaki, H. Tetrahedron Lett. 1983, 24, 2185; (i) Matsubara, S.; Takai, K.; Nozaki, H. ibid. 1983, 24, 3741; (j) Matsubara, S.; Takai, K.; Nozaki, H. Bull. Chem. Soc. Jpn. 1983, 56, 2029; (k) see ref. 6b; (l) Hayakawa, Y.; Uchiyama, M.; Noyori, R. Tetrahedron Lett. 1986, 27, 4195; (m) Curci, R.; Mello, R.; Troisi, L. Tetrahedron 1986, 42, 877; (n) Kanemoto, S.; Matsubara, S.; Takai, K.; Oshima, K.; Utimoto, K.; Nozaki, H. Bull. Chem. Soc. Jpn. 1988, 61, 3607; (o) Davis, F. A.; Lal, S. G.; Wei, J. Tetrahedron Lett., 1988, 29, 4269; (p) Olah, G. A.; Ernst, T. D. J. Org. Chem. 1989, 54, 1204; (q) Camporeale, M.; Fiorani, T.; Troisi, L.; Adam, W.; Curci, R.; Edwards, J. O. ibid. 1990, 55, 93; (r) Shibata, K.; Itoh, Y.; Tokitoh, N.; Okazaki, R.; Inamotc, N. Bull. Chem. Soc. Jpn. 1991, 64, 3749; (s) Chemla, F.; Julia, M.; Uguen, D. Bull. Soc. Chim. Fr. 1993, 130, 547; (t) Irie, R.; Hosoya, N.; Katsuki, T. Synlett 1994, 255; (u) Prouilhac-Cros, S.; Babin, P.; Bennetau, B.; Dunoguès, J. Bull. Soc. Chim. Fr. 1995, 132, 513; (v) Adam, W.; Korb, M. N. Tetrahedron, 1996, 52, 5487; (w) Adam, W.; Golsch, D.; Sundermeyer, J.; Wahl, G. Chem. Ber. 1996, 129, 1177; (x) Barton, D. H. R.; Chabot, B. M. Tetrahedron 1997, 53, 487; (y) Barton, D. H. R.; Chabot, B. M. ibid. 1997, 53, 511.

In addition to MTO, readily available inorganic rhenium oxides (e.g. $Re_2O_7$, $ReO_3(OH)$ and $ReO_3$) were found to exhibit high catalytic activity in the present system. FIG. 2 defines the scope of this new process with representative substrates including fairly unreactive olefins and/or progenitors of sensitive epoxides (The original MTO-based procedure Rudolph et al. *J. Am. Chem. Soc.* 1997, 119, 6189 remains superior for the preparation of highly acid-sensitive indene oxide). With the present protocol, terminal olefins and dienes, problematic in the original procedure, can be efficiently converted into the corresponding epoxides.

We discovered that when water (1 eq with respect to the olefin) is intentionally added at the beginning of the MTO-catalyzed epoxidation of cis-4-octene, BTSP is hydrolyzed within 10 minutes (as determined by GC), (Disappearance of BTSP in the course of the reaction can be conveniently monitored by gas chromatography) and poor conversions are observed presumably due to the sensitivity of the generated epoxidizing species to excess water (vide infra). In addition, significant amount of the diol originating from the epoxide ring-opening is formed. On the other hand, MTO-catalyzed epoxidations conducted in the presence of 4 Å molecular sieves are extremely slow. Control experiments demonstrate that MTO is not absorbed or inactivated by molecular sieves under these conditions, ruling out catalyst removal as the origin of lost activity. Similarly, very sluggish epoxidation is observed when $Re_2O_7$ is used as a catalyst for the epoxidation of 1-decene in anhydrous dichloromethane (ca. 7% conversion after 2.5 hours). The reaction is dramatically accelerated upon addition of 5 mol % water. On the basis of these observations one could propose that a trace of water in the reaction mixture hydrolyzes BTSP to hydrogen peroxide which subsequently adds to the rhenium center producing the peroxo complex while releasing a water molecule which closes the oxidant regeneration loop (FIG. 3).

In contrast to epoxidation with aqueous $H_2O_2$ where equilibrating bis- and monoperoxo complexes are produced instantaneously upon exposure of the catalyst to the oxidant, the reaction between equimolar amounts of MTO and BTSP has a considerable induction period under anhydrous conditions. We attribute this phenomenon to the necessity of "acidity build-up" (the water molecule coordinated to the rhenium center of the bisperoxo complex of MTO is highly acidic: Herrmann, W. A.; Fischer, R. W.; Marz, D. W. *Angew. Chem.* 1993, 103, 1991). Adventitious moisture can trigger an autocatalytic decomposition of an acid-sensitive BTSP into $H_2O_2$ and hexamethyldisilcoxane. Alternatively, partial hydrolysis of BTSP could afford $Me_3SiOOH$ which could act as an oxidant in the present system. For the use of silyl hydroperoxides in epoxidation, see: Dannley, R. L.; Jalics, G. J. *Org. Chem.* 1965, 30, 2417; Rebek, J.; McCready, R. *Tetrahedron Lett.* 1979, 4337.

The intrinsic "slow addition" of hydrogen peroxide to the oxorhenium precursor is managed by the "proton dependent" cycle shown in FIG. 3 which accomplishes transfer of the peroxo group from silicon to rhenium. In contrast, it is very difficult to exercize such control in the $H_2O_2$ (aqueous or anhydrous) MTO-catalyzed epoxidation processes; for example, slow addition of $H_2O_2$ does not help in achieving higher conversions due to faster catalyst decomposition at lower $H_2O_2$ concentrations (Ironically, MTO is stabilized at higher $H_2O_2$ concentrations: Herrmann, W. A.; Fischer, R. W.; Scherer, W.; Rauch, M. U. *Angew. Chem., Int. Ed. Engl.* 1993, 32, 1157).

Worthy of note, the aforementioned hydrolysis of BTSP to $H_2O_2$ is the simplest of many scenarios which could explain the requirement for $H_2O$. In a more general way, the need for a protic solvent is accommodated in FIG. 4b.

In accord with the previous observations, additives such as pyridines serve to prevent sensitive epoxide ring opening by buffering the highly acidic rhenium species. Notably, compared to the original system, the amount of ligand necessary to achieve the desired protection is now decreased from 12 to 0.5–1 mol % in both MTO and $Re_2O_7$-catalyzed epoxidations (The use of 12 mol % of pyridine completely arrested the reaction, presumably due to base-mediated decomposition of MTO). In some instances MTO loadings can be lowered to 0.25 mol % without affecting conversions—a manifestation of prolonged catalyst lifetime under the present conditions.

The use of $Re_2O_7$, $ReO_3(OH)$ and $ReO_3$ as catalyst precursors is a particularly important feature of the present protocol. Catalytic activities of these inorganic rhenium species for epoxidation with $H_2O_2$ were known to be very poor. For the epoxidation of $C_{2-20}$ olefins with stoichiometric $Re_2O_7$ in the presence of pyridine, see: Union Oil Co. of California (Fenton, D. M.) U.S. Pat. No. 3,316,279; (c) for early applications of $Re_2O_7$ in olefin/$H_2O_2$ oxidation catalysis see: duPont de Nemours and Co. (Parshall, G. W.) U.S. Pat. Nos. 3,657,292 and 3,646,130 (1972); (d) Warwel and co-workers found that $Re_2O_7$ is a more effective epoxidation catalyst if the right solvent is chosen. Their system employs 60% aqueous $H_2O_2$ in 1,4-dioxane at 90° C. and 1,2-diols are isolated in good yields, the initially formed epoxides being unstable in this system: Warwel, S.; Rüsch gen Klaas, M.; Sojka, M. *Chem. Commun.* 1991, 1578; (e) Herrmann, W. A.; Correia, J. D. G.; Kuhn, F. E.; Artus, G. R. J. *Chemistry—A European Journal* 1996, 2, 168.

Generally, the high acidity of these systems does not allow epoxides to be isolated except in special cases such as from cis-cyclooctene (which affords an epoxide which is particularly resistant to acid-catalyzed ring opening). In the present system, rhenium oxides are comparable and in some cases superior to MTO especially for the epoxidation of terminal olefins and dienes. The cost of the process can be significantly reduced by using these less expensive oxorhenium catalysts in combination with BTSP, now more available through improved preparations. MTO and $Re_2O_7$ were purchased from Strem Chemicals, Inc. $ReO_3$ and $HOReO_3$ were purchased from Aldrich Chemical and Co. For industrial sources of rhenium, see: Peacock, R. D. "The Chemistry of Technetium and Rhenium," Elsevier: Amsterdam, 1966.

This example illustrates improved conditions which were developed under which simple inorganic oxorhenium species act as efficient olefin epoxidation catalysts. It appears that the hydrolytic stability of MTO has been the sole reason for its better catalytic activity in the epoxidation so far. In conjunction with BTSP, which can be easily and economically prepared on a large scale, more readily accessible inorganic oxorhenium derivatives can now be applied; the parent MTO-catalyzed processes benefit from decreased catalyst loadings. In addition, the use of BTSP avoids hazards associated with highly concentrated $H_2O_2$ solutions. Thus, these rhenium catalyzed epoxidations continue to become more attractive for practical applications. In a more general sense, perhaps our finding can be utilized in other processes where lability of silicon-bound heteroatoms can effect often desired controlled release of reagents. Lastly, elimination of water from the reaction might lead to more pronounced influence of the external ligand on the reactivity in the present homogeneous epoxidation system. Perhaps, based on our study that emphasizes the importance of limited water content, new hydrogen peroxide-based epoxidations that incorporate continuous water removal throughout the process, thereby extending catalyst lifetime, will emerge.

EXAMPLE 2

Olefin Epoxidation with Bis(trimethylsilyl) Peroxide Catalyzed by Inorganic Oxorhenium Derivatives This example illustrates the systematic investigation of the oxorhenium catalyst precursors and the effects of various additives on the efficiency of olefin epoxidation with BTSP. Discovery of the beneficial effect of pyridine in the MTO-catalyzed epoxidation prompted our detailed study of this phenomenon with the goal of further improving the system. From the very beginning, salient features of the pyridine-modified protocol seemed counterintuitive. For example, base-mediated decomposition pathways of MTO in aqueous $H_2O_2$ have been established (Herrmann et al. used N-bases in order to suppress epoxide ring opening (Herrmann et al. *Angew. Chem. Int. Ed. Engl.* 1993, 103, 1991) albeit at the expense of detrimental effect on catalytic activity. For the most recent study of the MTO/Lewis base catalysts in olefin epoxidation, see: Herrmann et al. *J. Organomet. Chem.* 1997, 549, 319; For a comprehensive study on the base-induced decomposition of MTO, see Abu-Omar et al. *J. Am. Chem. Soc.* 1996, 118, 4966; in the presence of pyridine and $H_2O_2$, MTO is slowly oxidized, producing pyridinium perrhenate and $CH_{fl3}OH$: Yudin—unpublished results The hydroperoxide (HOO—) species induces the decomposition of MTO into methanol and catalytically inactive perrhenate (ReO₄—). Pyridine can be expected to facilitate this detrimental process by increasing the pH of the medium. Indeed, pyridinium perrhenate is formed during MTO-catalyzed epoxidations mediated by pyridine, but this does not adversely affect the epoxidations of most olefins, since full conversion is reached well before significant levels of catalyst decomposition are reached. Another important role attributed to pyridine in these systems is that of a buffer for the Lewis acidic Re(VII) species present, thereby enabling even sensitive epoxides to survive.

Despite the overall efficiency of the original pyridine-modified system, lower conversions were observed for less reactive substrates such as terminal olefins, due to the premature destruction of the catalyst. Although 3-cyanopyridine provided a remedy for this class of olefins, a more general way of extending catalyst lifetime became a challenge.

Among the known organometallic oxorhenium (VII) species (R—ReO₃) capable of catalyzing olefin epoxidation, MTO is most stable with respect to oxidative and/or hydrolytic removal of the alkyl group (vide infra). Hence, catalyst modification by variation of the R-substituent on the rhenium center was not rewarding despite extensive efforts in the Herrmann laboratory (Herrmann et al. *Inorg. Chem.* 1992, 31, 4431; for the most recent, and best, procedure, see: Herrmann et al. *Angew. Chem. Int. Ed. Engl.* 1997, 36, 2652). Elimination of water from the reaction would be an alternate path toward increased turnovers because catalyst decomposition should be largely suppressed. At the same time, the presence of pyridine should prevent the epoxide ring opening and, perhaps allow one to observe ligand effects on the selectivity features of the oxygen atom transfer event. A water-free environment should also eliminate possible complications from phase transfer effects.

Any process that involves $H_2O_2$ as the oxygen atom source produces at least one equivalent of water as by-product, which will defeat an anhydrous system unless an efficient water removal can be incorporated in the process design. A possible solution to the problem could be an oxidant that acts as an "anhydrous" analog of $H_2O_2$. Readily accessible bis(trimethylsilyl) peroxide (BTSP) has been previously used in this capacity. Cookson et al. *J. Organomet. Chem.* 1975, 99, C31; Taddei et al. *Synthesis* 1986, 633; for a convenient, large-scale (0.5 mol) preparation of BTSP from bis(trimethylsilyl)urea and urea/$H_2O_2$ complex in dichloromethane, see: Jackson, W. P. *Synlett* 1990, 536. The product obtained according to this method is virtually free of hexamethyldisiloxane, a common, albeit harmless, by-product in cognate BTSP preparations; Babin et al. *Synth. Commun.* 1992, 22, 2849. WARNING: Thermal stabilities of silylated organic peroxides have been studied: Vesnovskii, B. P.; Thomadze, A. V.; Suchevskaya, N. P.; Aleksandrov, Yu. A. *Zh. Priki. Khim.* 1982, 55, 1005. Pure BTSP has an active oxygen content of only 9% (cf. tert-butyl hydroperoxide—17.8%; di-tert-butyl peroxide—10.9%; hydrogen peroxide—47%). We would like to stress, however, that despite its great thermal stability, BTSP is subject to facile hydrolysis in the presence of water and acids which results in formation of hazardous 100% $H_2O_2$. Additionally, professors Henri Kagan and Dieter Seebach recently brought to our attention two reports from their respective laboratories that document explosions upon contact between BTSP and metal needles: Riant et al. *J. Org. Chem.* 1997, 62, 6733; Neumann et al. *Chem. Ber.* 1978, 111, 2785. Thus, only plastic or glass pipettes should be used to transfer BTSP.For applications of BTSP in organic synthesis, see: Brandes et al. *J. Organomet. Chem.* 1973, 49, C6; Brandes et al. ibid. 1974, 73, 217; Tamao et al. ibid. 1975, 94, 367; Salomon et al. *J. Am. Chem. Soc.* 1979, 101, 4290; Adam et al. *J. Org. Chem.* 1979, 44, 4969; Suzuki et al. ibid. 1982, 47, 902; eber, W. P. "Silicon Reagents in Organic Synthesis," Springwer-Verlag: New York, 1983; Kanemoto et al. *Tetrahedron Lett.* 1983, 24, 2185; Matsubara et al. ibid. 1983, 24, 3741; Matsubara et al. *Bull. Chem. Soc. Jpn.* 1983, 56, 2029; Kayakawa et al. *Tetrahedron Lett.* 1986, 27, 4195; Curci et al. *Tetrahedron* 1986, 42, 877; Kanemoto et al. *Bull. Chem. Soc. Jpn.* 1988, 61, 3607; Davis et al. *Tetrahedron Lett.* 1988, 29, 4269; Olah et al. *J. Org. Chem.* 1989, 54, 1204; Camporeale et al. ibid. 1990, 55, 93; Shibata et al. *Bull. Chem. Soc. Jpn.* 1991, 64, 3749. (s) Chemla et al. *Bull. Soc. Chim. Fr.* 1993, 130, 547; Irie et al. *Synlett* 1994, 255; Prouilhac-Cros et al. *Bull. Soc. Chim. Fr.* 1995, 132, 513; Adam et al. *Tetrahedron* 1996, 52, 5487; Adam et al. *Chem. Ber.* 1996, 129, 1177; Barton et al. *Tetrahedron* 1997, 53, 487; Barton et al. ibid. 1997, 53, 511.

To our surprise, however, MTO showed little to no reactivity toward BTSP in CDCl₃ (FIG. 1c) under stoichiometric conditions, (We felt that the substantial Lewis acidity of MeReO₃ would enable it to react with BTSP. Curci et al. has demonstrated that silylated peroxides are 50 to 100 times more effective than the corresponding hydrido analogs in electrophilic oxygen atom transfer to sulfides. Simple rate laws that do not require acid catalysis were deduced for these processes) in marked contrast to the reaction between MTO and aqueous $H_2O_2$ that instantaneously generates a mixture of mono- and bisperoxorhenium complexes. As previously reported by Curci et al., BTSP (ARCO Chemical Technology (Crocco et al., H. S.) U.S. Pat. No. 5,166,372 (1992)) is at least 50 times more reactive than $H_2O_2$ in stoichiometric oxidation of sulfides to sulfoxides which may account for the observed lack of nucleophilic reactivity of BTSP toward Re(VII) in the present system.

In the case of BTSP the expected formation of peroxo complexes must be accompanied by the silylation of the rhenium—bound oxo ligand (FIG. 4a, R=SiMe₃). This process is apparently much slower than its protic counterpart (FIG. 4a, R=H). Formation of the peroxo complexes in the MTO/BTSP system does occur, but only upon addition of an equivalent amount of water. Hydrolytic generation of $H_2O_2$ from BTSP accounts for this result and we subsequently established that a catalytic amount of MTO is sufficient to generate $H_2O_2$ in the BTSP/$H_2O$ system (BTSP is hydrolyzed to $H_2O_2$ within 2 hours in the presence of 1 eq $H_2O$ and 0.5 mol % MTO). Other proton sources (e.g. $CH_3OH$) are equally effective in promoting hydrolysis.

In accord with the aforementioned observations, no olefin epoxidation takes place in the MTO/BTSP system under water-free conditions. A trace of a protic species (e.g. water) is essential to enable rapid turnover of the catalytic cycle (An induction period can be attributed to the necessity of "acidity build-up". Adventitious moisture can trigger an autocatalytic decomoosition of acid-sensitive BTSP into $H_2O_2$ and hexamethyldisiloxane. Alternatively, partial hydrolysis of BTSP could afford $Me_3SiOOH$ which could act as an oxidant in the present system. For the use of silyl hydroperoxides in epoxidation, see: (a) Dannley, R. L.; Jalics, G. *J. Org. Chem.* 1965, 30, 2417. (b) Rebek, J.; McCready, R. *Tetrahedron Lett.* 1979, 20, 4337). The scenario shown in FIG. 3 involves the hydrolytic generation of free $H_2O_2$ from BTSP. Thus, intrinsic "slow addition" of hydrogen peroxide to the oxorhenium species is managed by the "proton dependent" cycle A (FIG. 3) which accomplishes transfer of the peroxo group from silicon to rhenium (cycle B). This represents a novel "controlled release" mode for the $H_2O_2$ addition in rhenium-catalyzed epoxidation processes. In contrast, it is impossible to exercise such control in $H_2O_2$ (aqueous or anhydrous) protocols (Ironically, MTO is stabilized at higher $H_2O_2$ concentrations: Herrmann et al. *Angew. Chem. Int. Ed. Engl.* 1993, 32, 1157). Slow addition of $H_2O_2$ does not help in achieving higher conversions due to faster MTO decomposition at lower $H_2O_2$ concentrations.

The most significant outcome of the limited water content in the present system is high catalytic epoxidation activity of inorganic high valent oxorhenium species. Thus, simple inorganic derivatives (e.g. $Re_2O_7$, $ReO_3(OH)$ and $ReO_3$) efficiently catalyze epoxidations with BTSP despite the well known hydrolytic instability of inorganic rhenium peroxides. Peroxo perrhenic acid ($H_4Re_2O_{13}$) was isolated in the $Re_2O_7/H_2O_2$ system as a highly hydrolytically labile, explosive compound: Herrmann et al. *Chemistry—A European Journal* 1996, 2, 168.

Although we have established that MTO catalyzes the generation of $H_2O_2$ from BTSP, the requirement for protic species in epoxidation can be explained by other closely related scenarios. Thus, in a more general way, the need for a proton source is accommodated in FIG. 4B where a regenerable XH species helps in ferrying the peroxo group from silicon to rhenium.

Having established the requirement for a proton source, we examined how the amount of such additive affects the reaction. For instance, reactivity was found to be a function of water concentration, and beyond a certain range (5–10 mol %) catalysis became inefficient, either due to the limited number of turnovers (cycle A) or due to the sensitivity of the catalytically active species to water. In fact, we noted that when excess water (1 eq relative to the olefin) is added at the beginning of the MTO-catalyzed epoxidation of cis-4-octene, BTSP is hydrolyzed within 10 minutes (as determined by GC), and poor conversions are observed. In addition, a significant amount of the diol, resulting from the hydrolytic ring opening of the epoxide, is formed. At the other extreme, efforts to remove all traces of water by running the process in the presence of 4 Å molecular sieves almost stop the epoxidation catalysis. Control experiments demonstrate that MTO is not absorbed or inactivated by the molecular sieves under these conditions, ruling out catalyst removal as the origin of lost activity. Similarly, very sluggish reaction takes place when $Re2O_7$ is used as a catalyst for the epoxidation of 1-decene under anhydrous conditions (ca. 7% conversion after 2.5 hours). The reaction is dramatically accelerated upon addition of 5 mol % water and reaches 70% completion within the next hour. It appears that the optimal water concentration range is 5–10 mol % depending on the substrate (vide supra).

The Role of Pyridine Derivatives and Other Additives. In accord with previous observations, additives such as pyridines serve to prevent sensitive epoxide ring opening by buffering the highly acidic rhenium species. Moreover, under present homogeneous conditions, the modulation of reactivity at the rhenium center is uncoupled from the phase transfer effects. Participation of water as a potential ligand is also minimized (Variable temperature NMR experiments indicate lability of the rhenium-bound pyridine ligands. Thus, $^1H$ NMR spectra of MTO in presence of 2 equivalents of pyridine are identical at −65° C. and at 25° C. and show one kind of pyridine species). Compared to the original system, the amount of the pyridine ligand that is necessary for the desired epoxide protection, is now decreased from 12 to 0.5–1 mol %. In the case of aqueous $H_2O_2$/MTO system, pyridine induces the formation of catalytically inactive perrhenic acid which results in lower turnovers for the less reactive substrates. In principle, inorganic oxorhenium catalysts should easily tolerate pH increase since no labile R-Re bond are present in the catalytically active species. At the same time, catalytic turnover in the present system crucially depends on efficient hydrolysis of BTSP and excess pyridine (10–12 mol %) dramatically slows down the reaction for all substrates. The optimal amount of the pyridine additive sufficient to maintain the epoxide protection is 0.5–1 mol % with minimal detrimental effect on the rate. We have also found that progenitors of highly sensitive epoxides do not tolerate even relatively low water concentrations. The preferred proton sources in such instances should contain conjugate bases of low nucleophilicity which do not participate in epoxide ring opening. In this regard, pyridinium trifluoroacetate was found to be particularly effective as a supplier of protons.

Catalyst Precursors. Comparable reactivity is observed among all inorganic oxorhenium derivatives (see FIG. 5). However, $ReO_3$ is preferred (at least for laboratory scale epoxidations) due to its non-hygroscopic nature relative to $Re_2O_7$. Unlike the rest of the precatalysts, $ReO_3$ does not dissolve in the reaction medium at the start. As the reaction proceeds, Re(VI) is rapidly oxidized to Re(VII), so that the solution acquires the bright yellow color characteristic of peroxorhenium(VII) species.

One of the most significant implications of the present controlled $H_2O_2$ release version of epoxidation is overall increase in the lifetime of oxorhenium catalysts. Indeed, hydrolytic removal of the methyl group from the rhenium center of the catalyst is no longer the origin of lost activity. Thus, the catalytically active species are preserved throughout the process and can be reused after evaporative removal of the solvent and the epoxide.

Substrate Scope. FIG. 5 defines the scope of this new process with representative substrates including fairly unreactive olefins and/or progenitors of sensitive epoxides. The optimal substrate concentration is in the 0.5–2M range with dichloromethane as solvent (Such species had long been known to exhibit weak activity as epoxidation catalysts: (a) for the epoxidation of $C_{2-20}$ olefins with stoichiometric $Re_2O_7$ in the presence of pyridine, see: Union Oil Co. of California (Fenton, D. M.) U.S. Pat. No. 3,316,279; for early applications of $Re_2O_7$ in olefin/$H_2O_2$ oxidation catalysis see: duPont de Nemours and Co. (Parshall, G. W.) U.S. Pat. Nos. 3,657,292 and 3,646,130 (1972); Warwel and co-workers found that $Re_2O_7$ is a more effective epoxidation catalyst if the right solvent is chosen. Their system employs 60% aqueous $H_2O_2$ in 1,4-dioxane at 90° C. and 1,2-diols are isolated in good yields, the initially formed epoxides being unstable in this system: Warwel, S.; Rüsch gen Klaas, M.; Sojka, M. *Chem. Commun.* 1991, 1578). No special precautions to exclude moisture during the reaction need to be taken. We stress, however, that because the catalytic turnover depends on the presence of protic additives and is inhibited at high water concentrations, it is good practice to account for any water beyond the deliberately added amount. With this in mind we recommend anhydrous dichloromethane. Upon completion of the reaction, the work-up procedure simply involves destruction of the traces of $H_2O_2$ with manganese dioxide and evaporation of dichloromethane and hexamethyldisiloxane ($Me_3SiOSiMe_3$, b.p. 100° C.).

With the present system, terminal olefins, problematic in the original procedure, are efficiently converted into the corresponding epoxides within short reaction times. Disubstituted olefins (both cis and trans) present little problem as do the tri- and tetrasubstituted olefins. However, in the latter two cases water has to be replaced by pyridinium trifluoroacetate as an external proton source (vide supra). Thereby, a conjugate base of lower nucleophilicity is involved which reduces the undesired epoxide ring opening. Notably, the original $H_2O_2$/pyridine system remains superior for the preparation of certain extremely acid-sensitive epoxides such as styrene oxide and indene oxide. Easily oxidizable substrates such as phenyl ethers are also beyond the scope of this new protocol due to the competitive oxidation of the aromatic ring.

Conditions were found under which simple inorganic oxorhenium compounds act, for the first time, as efficient olefin epoxidation catalysts (MTO and $Re_2O_7$ were purchased from Strem Chemicals, Inc. $ReO_3$ and $HOReO_3$ were purchased from Aldrich Chemical Co. For industrial sources of rhenium, see: Peacock, R. D. *The Chemistry of Technetium and Rhenium*; Elsevier: Amsterdam, 1966). The crucial factor enabling these inorganic oxorhenium species to exhibit high activity for epoxidation catalysis is thought to be the nearly anhydrous conditions which are achieved and maintained by using BTSP as the oxygen atom source, along with only a trace of a protic agent (e.g. $H_2O$) to catalyze slow transfer of the peroxide moiety from silicon to rhenium. If, as seems probable, BTSP becomes available on a large scale, this new "anhydrous" rheniumcatalyzed process could become one of the most reliable and convenient methods available for epoxidation of olefins at either laboratory or fine chemical production scales. In addition to the fact that the inexpensive, inorganic rhenium catalyst precursors are as effective as MTO, an especially attractive feature of these "anhydrous" systems is the simple work-up which entails only rotary evaporation of the dichloromethane and hexamethyldisiloxane from the reaction mixture.

While a preferred form of the invention has been shown in the drawings and described, since variations in the preferred form will be apparent to those skilled in the art, the invention should not be construed as limited to the specific form shown and described, but instead is as set forth in the following claims.

EXPERIMENTAL PROTOCALS

General $^1H$ and $^{13}C$ nmr spectra were recorded either on a Bruker AM-250, a Bruker AMX-400 or a Bruker AMX-500 spectrometer. Residual protic solvent $CHCl_3$ ($\delta_H$=7.26 ppm, $\delta_C$=77.0), $d_4$-methanol ($\delta_H$=3.30 ppm, $\delta_C$=49.0) and $D_2O$ ($\delta_H$=4.80 ppm, $\delta_C$ (of $\underline{C}H_3CN$)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel $F_{254}$) and visualized by cerium molybdophosphate or ninhydrin. Diethyl ether, tetrahydrofuran (THF) and toluene ($PhCH_3$) were distilled from sodium-benzophenone ketyl, dichloromethane (DCM) and acetonitrile from calcium hydride. Other solvents and reagents were purified by standard procedures if necessary.

General procedure for controlled water epoxidation using rhenium oxides as the catalyst and trialkylsilyl peroxides as the anhydrous oxidant as exemplified for mono, di, tri and tetra substituted olefins shown in FIG. 2, entries 1–8, FIG. 5, entries 1–11, and FIG. 6, entires 12–19; all listed olefins are purchase from Aldrich; since variations in the preferred form will be apparent to those skilled in the art, the invention should not be construed as limited to the specific compounds shown and described, but instead is as set forth in the following claims). In a 25 mL scintillation vial equipped with a magnetic stirrer, the olefin (1.41 g, 10 mmol) was placed followed by addition of 4 mL dichloromethane (the solvent is not limited to dichloromethane, but rather alternative solvents used in similar concentrations include: the solvent is selected from the group consisting of nitromethane ($CH_3NO_2$), nitroethane ($EtNO_2$), methylene chloride ($CH_2Cl_2$), chloroform ($CHCl_3$), carbon tetrachloride ($CCl_4$), 1,2-dichloroethane ($CH_2ClCH_2Cl$), pentachloroethane ($CCl_3CHCl_2$), chlorinated aromatic compounds: chlorobenzene, dichlorobenzene and other chlorinated solvents, fluorinated solvents and chlorofluoro hydrocarbons, acetonitrile ($CH_3CN$), acetone, benzene, toluene, xylenes, methanol, ethanol, propanol, isopropanol, butanol, t-butanol, ethyleneglycol, diethylether, THF (tetrahydrofuran) and supercritical $CO_2$). To this solution was added BTSP (2.8 g, 15 mmol; alternative related trialkylsilyl hydroperoxides used include $R_3SiOOH$ and polymeric derivatives ($-R_2SiOO-)_n$ (wherein in each case R=$C_1$–$C_6$alkyl); bis(tert-butyl)peroxide (Aldrich) and benzoyl peroxide (Aldrich) in combination with hexamethyldisilazane (Aldrich) (in situ source of BTSP eliminating the need for its isolation)). The vial was immersed into ice/water bath. After 5 minutes $Re_2O_7$ (24 mg, 0.05 mmol; alternative rhenium oxide catalysts used in the same concentration include: $RReO_3$ (wherein R=$C_1$–$C_6$alkyl for example, $CH_3ReO_3$), $Re_2O_7$, $ReO_3$, $HReO_4$, $NH_4ReO_4$, Re (metal), $ReO_2$ (All Aldrich), $Me_3SiOReO_3$) was added followed by 10 mL water. The reaction turned bright yellow and was allowed to warm up to room temperature and stirred for 14 h. Disappearance of BTSP in the course of the reaction was monitored by gas chromatography. Upon completion, water (3 drops) was added followed by manganese dioxide (ca. 5 mg) in order to decompose the remaining $H_2O_2$. The destruction of $H_2O_2$ was evident by the disappearance of yellow color. The mixture was then dried over $Na_2SO_4$. Concentration afforded the epoxide (1.48 g, 94% yield) of a colorless oil. Analytically pure sample is obtained by distillation. 4. The remaining 4% consisted of dichloromethane and traces (Ca. 2%) of haxamethyldisiloxane. 5. When the stock solution of $Re_2O_7$ in THF was used, stock solution of $Re_2O_7$ in THF (0.042 M) can be stored for weeks at room temperature with no signs of decomposition or lost activity in epoxidation. 6. if trans-Stilbene is used as the olefin, it is not completely dissolved at the beginning of the reaction. However, as the epoxidation proceeds, the mixture becomes homogeneous. Optional ligands which can be used to prevent sensitive epoxide ring opening include pyridine at concentrations from 0.25 mol % to 12 mol % and pyridine derivatives (same concentrations as pyridine if used in lieu of pyridine) containing electron withdrawing or electron donating groups (nitro, esters, ketones, halogens, nitriles, sulphonic acid esters), chiral pyridines (like cotinine), imines, oxazolines, 2-methylpyridine (2-picoline), 2-ethylpyridine, 2-propylpyridine, 2-phenylpyridine, 2-benzylpyridine, 2-fluoropyridine, 2-chloropyridine, 2-bromopyridine, 2-cyanopyridine, 2-hydroxypyridine, 2-pyridylcarbinol, 2-pyridineethanol, 2-pyridinepropanol, pyridine-2-carboxylic acid (picolinic acid) and corresponding esters, 3-methylpyridine (3-picoline), 3-ethylpyridine, 3-butylpyridine, 3-phenylpyridine, 3-benzylpyridine, 3-fluoropyridine, 3-chloropyridine, 3-bromopyridine, 3-cyanopyridine, 3-pyridylcarbinol, 3-hydroxypyridine, 3-pyridinepropanol, pyridine-3-carboxylic acid (nicotinic acid) and corresponding esters, 4-methylpyridine (4-picoline), 4-fluoropyridine, 4-chloropyridine, 4-bromopyridine, 4-cyanopyridine, 4-ethylpyridine, 4-isopropylpyridine, 4-t-butylpyridine, 4-(1-butylpentyl) pyridine, 4-phenylpyridine, 4-benzylpyridine, 4-(4-chlorobenzyl)pyridine, 4-hydroxypyridine, 4-methoxypyridine, 4-nitropyridine, pyridine-4-carboxylic acid and corresponding esters, 2,3-dimethylpyridine (2,3-lutidine), 2,4-dimethylpyridine (2,4-lutidine), 2,5-dimethylpyridine (2,5-lutidine), 2,6-dimethylpyridine (2,6-lutidine), 3,4-dimethylpyridine (3,4-lutidine), 3,5-dimethylpyridine (3,5-lutidine), 2,6-difluoropyridine, pentafluoropyridine, pentachloropyridine, 2,6-dichloropyridine, 3,5-dichloropyridine, 2,3,5-trichloropyridine, 3,4-dicyanopyridine, 5-chloro-3-pyridinol, 2,3-pyridinecarboxylic acid and corresponding esters, 2,4-pyridinecarboxylic acid and corresponding esters, 2,5-pyridinecarboxylic acid and corresponding esters, 2,6-pyridinecarboxylic acid and corresponding esters, 2,6-diphenylpyridine, 2,6-di-p-tolylpyridine, 3,4-pyridinecarboxylic acid and corresponding esters, 2-pyridineethansulfonic acid, 4-pyridineethanesulfonic acid, 2,3-cyclopentenopyridine, 2,3-cyclohexenopyridine, 2,3-cycloheptenopyridine, 2,4,6-collidine, pyrazine, 2,3-pyrazinedicarbonitrile, pyrazinecarbonitrile, 2,6-dichloropyrazine, pyrazinecarboxylic acid and corresponding esters, 2,3-dimethylpyrazine, 2,5-dimethylpyrazine, 2,6-dimethylpyrazine, 2,3-di-2-pyridylpyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinoL, 1,3,5-triazine, (−)-cotinine (1-methyl-5-(3-pyridyl)-2-pyrrolidinone) pyridine-2,6-dicarboxylic acid and corresponding esters, quinoline, isoquinoline, 2,2'-pyridyl, 2,2'-dipyridyl, 6-chloro-2,2'-bipyridine, 2,4'-dipyridyl, 4,4'-dipyridyl, 2,2':6',2"-terpyridine, 1,7-phenanthroline, 1,10-phenanthroline, 4,7-phenanthroline, phenazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-nitropyrazole, 2,5-diphenyloxazole, 2,4,5-trimethyloxazole, 2,4,4-trimethyl-2-oxazoline, 3,5-dimethylisoxazole, 2,6-bis[(4S)-isopropyl-2-oxazolin-2-yl]pyridine, 1,2-dimethylimidazole, 1-butylimidazole, 2,3,3-trimethylindolenine, caffeine, and polymer-supported ligands.

Standard Procedure for Preparation of Bis(trimethylsilyl) Peroxide (BTSP) on a 1 mol scale.

Finely powdered urea/$H_2O_2$ complex (94 g, 1 mol) was suspended in anhydrous dichloromethane (500 mL) in a 1 L oven-dried round-bottom flask equipped with a magnetic stirrer. To this mixture was added bis(trimethylsilyl)urea (204 g, 1 mol). A reflux condenser was attached and the flask was immersed into an oil bath maintained at 65–70° C. overnight. The liquid phase was distilled off (10 mm Hg) into an oven-dried round bottom 1 L flask maintained at −78° C. leaving slightly yellow urea residue. Due to partial occlusion of the product in this residue, it was further subjected to high vacuum bulb-to-bulb distillation. Finally, combined fractions were redistilled (10 mm Hg) using a short-path distillation head giving BTSP (133 g, 96% pure,[4] 75% yield) that was used for epoxidations without further purification.

Standard Procedure for Preparation of $R_3SiOOH$.

Finely powdered urea/$H_2O_2$ complex (1 eq) was suspended in anhydrous dichloromethane in a 1 L oven-dried round-bottom flask equipped with a magnetic stirrer. To this mixture was added trialkylsilyl chloride $R_3SiCl$ (1 eq; R=$C_1$–$C_6$alkyl; commerically available reagents from companies such as Aldrich). A reflux condenser was attached and the flask was immersed into an oil bath maintained at 65–70° C. overnight. Extraction with dichloromethane was followed by drying over anhydrous sodium sulfate. Evaporation of dichloromethane yielded $R_3SiOOH$ as an analytically pure material.

Standard Procedure for Preparation of Polymeric Derivatives (—$R_2SiOO$—)$_n$ (R=organic functionality; eg. $C_1$–C6alkyl)

Finely powdered urea/$H_2O_2$ complex (1 eq) was suspended in anhydrous dichloromethane in a 1 L oven-dried round-bottom flask equipped with a magnetic stirrer. To this mixture was added dimethyldichlorosilane (1 eq). A reflux condenser was attached and the flask was immersed into an oil bath maintained at 65–70° C. overnight. Extraction with dichloromethane was followed by drying over anhydrous sodium sulfate. Evaporation of dichloromethane yielded (—$R_2SiOO$—)$_n$ as a white solid.

Standard procedure for epoxidation on a 10 millimol scale in dichloromethane exemplified for 1-decene.

In a 25 mL scintillation vial equipped with a magnetic stirrer, 1-decene (1.41 g, 10 mmol) was placed followed by addition of 4 mL dichloromethane. To this solution was added BTSP (2.8 g, 15 mmol). The vial was immersed into ice/water bath. After 5 minutes $Re_2O_7$ (24 mg, 0.05 mmol)[5] was added followed by 10 µL of water. The reaction turned bright yellow and was allowed to warm up to room temperature and stirred for 14 h. Upon completion, water (3 drops) was added followed by manganese dioxide (ca. 5 mg) in order to decompose the remaining $H_2O_2$. The destruction of $H_2O_2$ was evident by the disappearance of yellow color. The mixture was then dried over $Na_2SO_4$. Concentration afforded 1-decene oxide (1.48 g, 94% yield) of a colorless oil.

Standard procedure for epoxidation on a 10 millimol scale in THF exemplified for trans-stilbene.

In a 25 mL scintillation vial equipped with a magnetic stirrer, trans-stilbene (1.80 g, 10 mmol) was placed followed by addition of 2.8 mL THF.[6] To this solution was added BTSP (2.8 g, 15 mmol). The vial was immersed into ice/water bath. After 5 minutes $Re_2O_7$ (24 mg, 0.05 mmol) was added dropwise as a solution in 1.2 mL THF.[7] The reaction turned yellow and was allowed to warm up to room temperature and stirred for 10 h. Upon completion, water (3 drops) was added followed by manganese dioxide (ca. 5 mg) in order to decompose the remaining $H_2O_2$. The destruction of $H_2O_2$ was evident by the disappearance of yellow color. The mixture was then dried over $Na_2SO_4$. Concentration afforded trans-stilbene oxide (1.88 g, 96% yield) of as an off-yellow solid.

The Boiling reactor process:

This process comprises a method which continuously removes water in the vapor stream by using appropriate solvent, temperature, and pressure conditions, keeping the concentration of the liquid phase low enough to maintain the activity of the oxorhenium catalyst. The method is as follows:

A 500 mL autoclave-type reaction vessel equipped with the liquid inlet (at the bottom) and gas outlet (on top) was charged with the rhenium precursor (such as $Re_2O_7$), olefin, and pyridine. The reactor was closed and heated as hydrogen peroxide dissolved in organic solvent such as tert-butanol was slowly added through a liquid inlet. As the reaction, maintained at the solvent reflux temperature, proceeded, water was being collected at the vapor outlet in the form of an azeotrope with organic solvent. To keep the concentration of the catalytic species constant with respect to the catalyst, olefin, pyridine, and epoxide, the solvent that was collected at the outlet in the form of azeotrope with water was passed through the drying agent and reintroduced at the bottom. This mode of operation allowed to continuously remove water in the vapor stream by using appropriate solvent, temperature, and pressure keeping the concentration of the liquid phase low enough to maintain the activity of the oxorhenium catalyst. At the end of the reaction, the volatiles (mainly the product epoxide) were removed and the rhenium catalyst was recycled in another run that revealed no loss of catalytic activity.

What is claimed is:

1. An improved process for epoxidizing an olefin by rhenium-catalysis, the process being of a type wherein a reaction mixture is formed by combining the olefin with a ligand, an oxidant, an organic solvent, a protic solvent and a catalytic organo or inorgano rhenium oxide under conditions suitable for epoxide formation to occur, wherein the improvement comprises:

said oxidant is a silicon based anhydrous oxidant and said oxidant is combined with the reaction mixture by a controlled slow addition, wherein the slow controlled addition of the silicon based anhydrous oxidant causes a transfer of a peroxo group from the oxidant to the rhenium oxide with the assistance of the protic solvent, thereby controlling excess water concentration and maximizing monoperoxocomplex formation.

2. The process as described in claim 1 wherein the silicon based anhydrous oxidant is a trialkylsilyl peroxide represented by the formulas $(R)_3SiOOSi(R)_3$, and $(—(R)_2SiOO—)_n$ wherein R is selected from the group consisting of $C_1$–$C_6$ alkyl and tert-$C_1$–$C_6$ alkyl.

3. The process as described in claim 2 wherein the silicon based anhydrous oxidant is bis(trimethylsilyl)peroxide.

4. The process as described in claim 2 employing the further addition to the reaction mixture of a water removal agent.

5. The process as described in claim 4 wherein the water removal agent is selected from the group consisting of Molecular sieves, $MgSO_4$, $Na_2SO_4$, $CaSO_4$, $CaCl_2$, $K_2CO_3$, CaO, $P_2O_5$.

6. The process as described in claim 1 wherein the rhenium catalyst is selected from the group consisting of $(R)ReO_3$, $Re_2O_7$, $ReO_3$, $ReO_3(OH)$, $HReO_4$, $NH_4ReO_4$, Re (metal), $ReO_2$, and $Me_3SiOReO_3$ wherein R is selected from the group consisting of $C_1$–$C_6$ alkyl and tert-$C_1$–$C_6$ alkyl.

7. The process as described in claim 1 with the following additional step: removing product water formed during the reaction process by a boiling reactor for maintaining an aqueous concentration in the reaction mixture low enough for retaining activity of the oxorhenium catalyst.

8. The process as described in claim 1 wherein the olefin is a mono-substituted olefin.

9. The process as described in claim 1 wherein the olefin is a di-substituted olefin.

10. The process as described in claim 1 wherein the olefin is a tri-substituted olefin.

11. The process as described in claim 1 wherein the olefin is a tetra-substituted olefin.

12. The process as described in claim 1 wherein the ligand is selected from the group consisting of pyridine, pyridine derivatives containing electron withdrawing or electron donating groups (nitro, esters, ketones, halogens, nitriles, sulphonic acid esters), chiral pyridines (like cotinine), imines, oxazolines, 2-methylpyridine (2-picoline), 2-ethylpyridine, 2-propylpyridine, 2-phenylpyridine, 2-benzylpyridine, 2-fluoropyridine, 2-chloropyridine, 2-bromopyridine, 2-cyanopyridine, 2-hydroxypyridine, 2-pyridylcarbinol, 2-pyridineethanol, 2-pyridinepropanol, pyridine-2-carboxylic acid (picolinic acid) and corresponding esters, 3-methylpyridine (3-picoline), 3-ethylpyridine, 3-butylpyridine, 3-phenylpyridine, 3-benzylpyridine, 3-fluoropyridine, 3-chloropyridine, 3-bromopyridine, 3-cyanopyridine, 3-pyridylcarbinol, 3-hydroxypyridine, 3-pyridinepropanol, pyridine-3-carboxylic acid (nicotinic acid) and corresponding esters, 4-methylpyridine (4-picoline), 4-fluoropyridine, 4-chloropyridine, 4-bromopyridine, 4-cyanopyridine, 4-ethylpyridine, 4-isopropylpyridine, 4-t-butylpyridine, 4-(1-butylpentyl) pyridine, 4-phenylpyridine, 4-benzylpyridine, 4-(4-chlorobenzyl)pyridine, 4-hydroxypyridine, 4-methoxypyridine, 4-nitropyridine, pyridine-4-carboxylic acid and corresponding esters, 2,3-dimethylpyridine (2,3-lutidine), 2,4-dimethylpyridine (2,4-lutidine), 2,5-dimethylpyridine (2,5-lutidine), 2,6-dimethylpyridine (2,6-lutidine), 3,4-dimethylpyridine (3,4-lutidine), 3,5-dimethylpyridine (3,5-lutidine), 2,6-difluoropyridine, pentafluoropyridine, pentachloropyridine, 2,6-dichloropyridine, 3,5-dichloropyridine, 2,3,5-trichloropyridine, 3,4-dicyanopyridine, 5-chloro-3-pyridinol, 2,3-pyridinecarboxylic acid and corresponding esters, 2,4-pyridinecarboxylic acid and corresponding esters, 2,5-pyridinecarboxylic acid and corresponding esters, 2,6-pyridinecarboxylic acid and corresponding esters, 2,6-diphenylpyridine, 2,6-di-p-tolylpyridine, 3,4-pyridinecarboxylic acid and corresponding esters, 2-pyridineethansulfonic acid, 4-pyridineethanesulfonic acid, 2,3-cyclopentenopyridine, 2,3-cyclohexenopyridine, 2,3-cycloheptenopyridine, 2,4,6-collidine, pyrazine, 2,3-pyrazinedicarbonitrile, pyrazinecarbonitrile, 2,6-dichloropyrazine, pyrazinecarboxylic acid and corresponding esters, 2,3-dimethylpyrazine, 2,5-dimethylpyrazine, 2,6-dimethylpyrazine, 2,3-di-2-pyridylpyrazine, pyridazine, 3-methylpyridazine, 4-methylpyridazine, pyrimidine, 4-methylpyrimidine, 4,6-dimethylpyrimidine, 4-phenylpyrimidine, 2,4-dichloropyrimidine, 4,6-dichloropyrimidine, 2,4,5-trihydroxypyrimidine, 4-(trifluoromethyl)-2-pyrimidinol, 1,3,5-triazine, (−)-cotinine (1-methyl-5-(3-pyridyl)-2-pyrrolidinone) pyridine-2,6-dicarboxylic acid and corresponding esters, quinoline, isoquinoline, 2,2'-pyridyl, 2,2'-dipyridyl, 6-chloro-2,2'-bipyridine, 2,4'-dipyridyl, 4,4'-dipyridyl, 2,2':6',2"-terpyridine, 1,7-phenanthroline, 1,10-phenanthroline, 4,7-phenanthroline, phenazine, 3,6-di-2-pyridyl-1,2,4,5-tetrazine, 2,2'-bipyridine-4,4'-carboxylic ester, 1,2-bis(4-pyridyl)ethane, 4,4'-trimethylenepyridine, quinoxaline, 2,3-dimethylquinoxaline, 1-nitropyrazole, 2,5-diphenyloxazole, 2,4,5-trimethyloxazole, 2,4,4-trimethyl-2-oxazoline, 3,5-dimethylisoxazole, 2,6-bis[(4S)-isopropyl-2-oxazolin-2-yl]pyridine, 1,2-dimethylimidazole, 1-butylimidazole, 2,3,3-trimethylindolenine, and caffeine.

13. The method as described in claim 1 wherein the solvent is selected from the group consisting of nitromethane ($CH_3NO_2$), nitroethane ($EtNO_2$), methylene chloride ($CH_2Cl_2$), chloroform ($CHCl_3$), carbon tetrachloride ($CCl_4$), 1,2-dichloroethane ($CH_2ClCH_2Cl$), pentachloroethane ($CCl_3CHCl_2$), chlorinated aromatic compounds: chlorobenzene, dichlorobenzene and other chlorinated solvents, fluorinated solvents and chlorofluoro hydrocarbons, acetonitrile ($CH_3CN$), acetone, benzene, toluene, xylenes, methanol, ethanol, propanol, isopropanol, butanol, t-butanol, ethyleneglycol, diethylether, THF (tetrahydrofuran) and supercritical $CO_2$.

14. The process as described in claim 1 wherein the ligand is present in 0.25 to 1.0 mol % overall concentration.

15. The process as described in claim 1 wherein the ligand is present in 0.25 to 12.0 mol % overall concentration.

16. The process as described in claim 1 wherein the overall water concentration is within the range of 0.5–80.0 mol %.

* * * * *